(12) United States Patent
Kawada

(10) Patent No.: US 6,352,693 B1
(45) Date of Patent: Mar. 5, 2002

(54) POISON BAIT COMPOSITIONS

(75) Inventor: Hitoshi Kawada, Funabashi (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/286,985

(22) Filed: Apr. 7, 1999

(30) Foreign Application Priority Data

Apr. 10, 1998 (JP) .............................. 10-099616

(51) Int. Cl.$^7$ .................. A01N 25/00; A01N 25/04; A01N 31/02; A01N 57/14

(52) U.S. Cl. ................ 424/84; 424/405; 514/54; 514/132; 514/738; 514/777; 514/782; 514/944

(58) Field of Search ............... 424/84, 405; 514/777, 514/782, 54, 132, 738, 944

(56) References Cited

U.S. PATENT DOCUMENTS 5,950,360 A * 9/1999 Heinrich et al. ............. 47/58.1

FOREIGN PATENT DOCUMENTS

| EP | 084 310 | 7/1983 |
|---|---|---|
| WO | WO 91/07972 | 6/1991 |

OTHER PUBLICATIONS

WPIDS Abstract 1972–42455T, abstracting JP 47–23198.*
Chemical Abstracts 68:47433, 1968.*
Chemical Abstracts 118: 2475n, 1993.*
The Merck Index 10$^{th}$ edition, Merck & Co., Inc., Rahway, NJ, p. 644, entry no. 4347, 1983.*
Chemical Abstracts, Abstract No. 124:79465, Abstract of JP 070258015, Oct. 9, 1995.
Chemical Abstracts, Abstract No. 122:284623, Abstract of JP 070033608, Feb. 3, 1995.
Chemical Abstracts, Abstract No. 117:228476, Abstract of JP 040134002, Jul. 5, 1992.
WPI Abstract Accession No. 92–204452/25, Abstract of JP 040134002, Jul. 5, 1992.
Chemical Abstracts, Abstract No. 112:231341, Abstract of JP 010197402, Aug. 9, 1989.
WPI Abstract Accession No. 78–22980A/25, Abstract of JP 520021187, Feb. 17, 1977.

* cited by examiner

*Primary Examiner*—John Pak
(74) *Attorney, Agent, or Firm*—Sughrue Mion, PLLC

(57) ABSTRACT

An effective poison bait composition is provided for the control of such objective pests as cockroaches, wherein the poison bait composition comprises (1) a pesticidally effective amount of a pesticidally active ingredient, (2) a carrageenan, and (3) glycerin. A methods of controlling objective pests is also provided, which utilizes the provided poison bait.

10 Claims, No Drawings

POISON BAIT COMPOSITIONS

FIELD OF THE INVENTION

The present invention relates to poison bait compositions that control pests and to methods of controlling pests.

BACKGROUND OF THE INVENTION

Poison bait compositions are well known as being useful in controlling pests such as cockroaches, ants and the like. Such poison bait compositions typically contain an edible composition that provides control over the pest after said pest has ingested the poison bait. Since the poison bait compositions also generally contain a pesticidal compound, there is typically a greater pest controlling activity associated with said baits when large quantities of pests ingest said baits, and conversely a smaller pest controlling activity when a smaller quantity of pests ingest said baits.

WO 91-7972, describes an insect bait that comprises carrageenan as an insect attractant. The insect bait set forth in said description, however, is deficient in that said insect bait fails to control a sufficient amount of pests when the employed to control pests.

SUMMARY OF THE INVENTION

The present invention provides for a poison bait composition that can serve to effectively control large quantities of pests, including cockroaches, ants and the like. Specifically, such pests are brought under control after the poison bait composition has been employed to control pests, based on the superior pest controlling activity of the poison bait. More specifically, by having a large quantity of pests ingest effective amounts of the poison bait of the present invention, a pesticidally active ingredient in the poison bait results in a superior pest controlling activity over objective pests.

A poison bait of the present invention comprises (1) a pesticidally active ingredient, (2) a carrageenan and (3) glycerin, and may further comprise optional ingredients such as fats, fatty oils, powdered crops, dextrin, sugars, synergists, other additive ingredients well known to those skilled in the art, and mixtures thereof.

The pesticidally active ingredient, carrageenan and glycerin components of the inventive poison bait compositions generally provide the poison bait compositions of the present invention with the ability to provide superior control over objective pests, over which control is desired. As such, the poison bait compositions of the present invention are also useful in allowing the Inventor to provide an advantageous method of controlling objective pests.

DETAILED DESCRIPTION OF THE INVENTION

The poison bait compositions of the present invention comprise (1) a pesticidally active ingredient, (2) a carrageenan, and (3) glycerin, and optionally therewith may contain synergistic agent(s), powdered crops, dextrin, sugars, fats and/or fatty oils, and other additives typically used by those skilled in the art (such as those disclosed hereinbelow), and mixtures thereof The pesticidally effective amount of the pesticidally active ingredient that is present in the poison bait compositions of the present invention depends on the specific type of said pesticidally active ingredient used in the poison bait compositions, but generally the amount of the pesticidally active ingredient in the provided poison bait composition is from about 0.05% to 10% by weight, based on the total weight of the provided poison bait composition. Typical examples of the pesticidally active ingredient include, pyrethroid compounds, organophosphorus compounds, carbamate compounds, N-aryldiazole compounds, hydrazone compounds, sulfonamide compounds, naturally occurring pesticidal compounds, boric acids, juvenile hormone analogues, chitin synthesis inhibitors, and the like.

Exemplarily of the variety of pesticidally active compounds that may be used in the present inventive poison bait compositions are the following: 5-benzyl-3-furylmethyl chrynsathemate, 3,4,5,6-tetrahydrophthalimidomethyl chrysanthemate, 3-phenoxybenzyl chrysanthemate, 3-phenoxybenzyl 3-(2,2-dichlorovinyl)-2,2-dimethylcyclopropanecarboxylate, 2-methyl4-oxo-3-(2-propenyl)cyclopent-2-enyl chrysanthemate, 2-methyl-4-oxo-3-(2-propynyl)cyclopent-2-enyl chrysanthemate, 2-methyl-4-oxo-3-(2-propenyl)cyclopent-2-enyl 2,2,3,3-tetramethylcyclopropanecarboxylate, 1-ethynyl-2-methyl-2-pentenyl chrysanthemate, 2,3,5,6-tetrafluorobenzyl 3-(2,2-dichlorovinyl)-2,2-dimethylcyclopropanecarboxylate, 2,3,5,6-tetrafluoro-4-methylbenzyl 3-(2,2-dichlorovinyl)-2,2-dimethylcyclopropanecarboxylate, α-cyano-3-phenoxybenzyl chrysanthemate, αcyano-3-phenoxybenzyl 2,2-dimethyl-3-(1,2,2,2-tetrabromoethyl) cyclopropanecarboxylate, α-cyano-3-phenoxybenzyl 2-(4-chlorophenyl)-3-methylbutyrate, α-cyano-3-phenoxybenzyl 2,2,3,3-tetramethylcyclopropanecarboxylate, α-cyano-3-phenoxybenzyl 3-(2,2-dichlorovinyl)-2,2-dimethylcyclopropanecarboxylate, α-cyano-3-phenoxybenzyl 2-(2-chloro-4-trifluoroanilino)-3-methylbutyrate, 2-(4-ethoxyphenyl)-2-methylpropyl 3-phenoxybenzyl ether, O,O-dimethyl O-(3-methyl-4-nitrophenyl) phosphorothioate (fenitrothion), 2,2-dichlorovinyl dimethyl phosphate, O,O-diethyl O-(2-isopropyl-6-methyl-4-pyrimidinyl) phosphorothioate, (E)-O-2-isopropoxycarbonyl-1-methylvinyl O-methyl ethylphosphoroamidothioate, O,O-diethyl O-(3,5,6-trichloro-2-pyridyl) phosphorothioate, O,O-dimethyl O-(3, 5,6-trichloro-2-pyridyl) phosphorothioate, S-6-chloro-2,3-dihydro-2-oxo-1,3-oxazolo[4,5-b]pyridin-3-ylmethl O,O-dimethyl phophorothioate, 5-methoxy-3-(2-methoxyphenyl)-1,3,4-oxadiazol-2(3 H)-one, 2-(1-methylethoxy)phenyl methylcarbamate, 1-naphthyl methylcarbamate, 4-(2-bromo-1,1,2,2-tetrafluoroethyl)-1-(3-chloro-5-trifluoromethylpyridin-2-yl)-2-methylimidazole, tetrahydro-5,5-dimethyl-2(1H)-pyrimidinone[[3-(trifluoromethyl)phenyl]-1-[2-[4-(trifluoromethyl)phenyl]ethenyl]-2-propenylidene] hydrazone, N-ethyl perfluoro-octanesulfonamide, abamectine, boric acid, 2-[1-methyl-2-(4-phenoxyphenoxy) ethoxy]pyridine, isopropyl 11-methoxy-3,7,11-trimethyldodeca-2,4-dienonate, ethyl 3,7,11-trimethyldodeca-2,4-dienonate, 1-(4-chlorophenyl)-3-(2,6-difluorobenzoyl)urea, 1-(3,5-dichloro-2,4-difluorophenyl)-3-(2,6-difluorobenzoyl)urea, 1-(4-trifluoromethoxyphenyl)-3-(2-fluorobenzoyl)urea, N-cyclopropyl-1,3,5-triazine-2,4, 6-triamine, 2-t-butylimino-3-isopropyl-5-phenylperhydro-1, 3,5-thiadiazin-4-one, and active isomers thereof.

The poison bait compositions of the present invention also comprise a carrageenan therein in an amount from about 1% to 10% by weight, based on the total weight of the provided poison bait composition. The carrageenan is preferably a galactan, and more preferably comprises a sulfate group. Such carrageenans are typically products that can be extracted from plants such as Rhodophyceae. In addition, the poison bait compositions of the present invention may comprise various forms of the carrageenan component therein, such as commercially available kappa (κ), lambda (λ) and iota (ι) isomers. Even so, it is preferable that a poison bait composition of the present invention comprise a κ-carrageenan isomer as the carrageenan, since it is believed that a larger quantity of pests will ingest a pesticidally effective amount of said poison bait composition, when said compositions comprise a κ-carrageenan.

A poison bait composition of the present invention also comprises glycerin, preferably in an amount from about 1% to 10% by weight, based on the total weight of the poison bait composition. The glycerin can be a commercially available glycerin, if so desired, and when chosen as such, can be utilized without further purification.

If so desired, the poison bait compositions of the present invention may optionally comprise fats, fatty oils, powdered crops, dextrin, sugars or mixtures thereof, such that the total amount of such ingredients in the provided poison bait composition is from about 40% to 85% by weight, based on the total weight of the poison bait composition. The fats utilized in the present invention are aliphatic hydrocarbons that are typically in a solid phase at room temperature, whereas the fatty oils utilized in the present invention are typically aliphatic hydrocarbons that are in a liquid phase at room temperature. Examples of such fats include butter, margarine, peanut butter and the like. Examples of such fatty oils include aliphatic oils, and more specifically, plant oils such as sesame oil, soy oil, rape seed oil, wheat germ oil, cotton seed oil, corn oil, sunflower oil, palm oil, mixtures thereof and the like. When powdered crops are incorporated into the present inventive poison bait compositions, they are usually crops that are in a powder form or an extraction of a starch from said crops, with examples of such powdered crops including starches of maize, potatoes, sweet potatoes, cereals or the like, flours, ricemeal, cornmeal, potatomeal, the powder of other grains that are edible to pests, and mixtures thereof Dextrin, which is a glucose polymer in the hydrolysis of starch, when incorporated in the present inventive compositions, may be obtained from the hydrolysis of starches, which have traditionally been obtained from maize, potato, sweat potato, wheat, rice or the like by the use of acids, heat or amylases. Sugars, which are carbohydrate compounds that may be utilized in the present inventive compositions, are usually soluble in water, and are exemplified by sucrose, glucose, fructose granulated sugars, fructose, lactose, raw sugar, brown sugar, molasseses, mixtures thereof and the like.

The poison bait compositions of the present invention preferably comprise at least one ingredient selected from the group consisting of fats and fatty oils, in combination with at least one ingredient selected from the group consisting of powdered crops, dextrin, and sugars. In such a case, the amount of the fats and/or fatty oils is usually from about 5% to 20% by weight and the amount of the powdered crops, dextrin and/or sugars is from about 30% to 80% by weight, based on the total weight of the provided poison bait composition.

In addition, the poison bait compositions of the present invention may also optionally comprise a synergist such as α-[2-(2-butoxyethoxy)ethoxy]-4,5-methylenedioxy-2-propyltoluene, octachlorodipropyl ether, isobornyl thiocyanatoacetate and N-(2-ethylhexyl)bicyclo[2.2.1]hept-5-en-2,3-dicarboxyimide, to enhance the pest controlling efficacy of the pesticidally active ingredient, so that the combined effect of both the synergist and said pesticidally active ingredient is greater than a product that comprises either individually. When present, the synergist should be utilized in an effective synergy producing amount in the inventive poison bait compositions.

In addition, the poison bait compositions of the present invention may also optionally comprise other additive ingredients that are well known to those skilled in the art, such as antioxidants, preservatives, agents which prevent erroneous ingestion, fillers and flavorings. Antioxidants that may be included in the poison bait compositions of the present invention are antioxidants which prevent harmful oxidation of any component contained in the poison bait compositions from the environment, so that the poison bait compositions may sustain a more effective formulation for a longer period of time. Examples of such antioxidants that may be incorporated into the poison bait compositions of the present invention include erythorbic acid, sodium erythorbate, dibutylhydroxytoluene, α-tocopherol, nordihydroguaiaretic acid, methylhydroxyanisole, propyl gallate, guaiacum, L-cysteine hydrochloride and the like. The preservatives, which may be included in the poison bait composition of the present invention, can be utilized to decelerate the deterioration of the poison bait compositions, and more specifically, may prevent troublesome microbes from being notably prolific on the poison bait compositions. Examples of suitable preservatives that may be included in the poison bait compositions include benzoic acid, sodium benzoate, salicylic acid, sorbic acid, potassium sorbate, dehydroacetic acid, sodium dehydroacetate, isobutyl paraoxybenzoate, isopropyl paraoxybenzoate, ethyl paraoxybenzoate, butyl paraoxybenzoate, propyl parahydroxybenzoate, calcium propionate, sodium propionate and the like. The agents which prevent erroneous ingestion and/or help to avert ingestion of one of the inventive poison bait compositions by children or pets (which are never intended to feed on the inventive poison bait composition) include red pepper powder, amaranth, amaranth aluminum lake, erythrosine, erythrosine aluminum lake, new coccine, phloxine, rose bengal, acid red, tartrazine, tartrazine aluminum lake, sunset yellow FCF, sunset yellow FCF aluminum lake, fast green FCF, fast green FCF aluminum lake, brilliant blue FCF, brilliant blue FCF aluminum lake, indigocarmine, indigocarmine aluminum lake, β-carotene, copper chlorophyll and the like. The poison bait compositions of the invention may also comprise fillers which allow a formulation of the poison bait composition to be handled more easily than a formulation that does not comprise a filler. Examples of such fillers that may be incorporated into the inventive poison bait compositions include white carbon, diatomaceous earth, crystalline cellulose, kaolin, talc, bentonite, zeolite, sepiolite, attapulgite and the like. The flavorings that may also be optionally contained in the present inventive compositions, can also be components that result in the inventive poison bait compositions being more edible to pests, if so desired. Examples of such flavorings including cheese flavoring, butter flavoring, peanut flavoring, peach flavoring, strawberry flavoring, milk flavoring and the like.

The poison bait compositions of the present invention may be formulated into various formulation types, with examples of such formulation types including dusts, pastes, granules, tablets and other similar formulations well known to those skilled in the art, provided that the objective pests can still consume the poison bait composition of the present invention in the provided formulation. A dust poison bait formulation of the present invention may be prepared by mixing and optionally pulverizing the respective ingredients of one of the poison bait compositions of the invention. A formulation of one of the inventive poison bait pastes or granules, may be obtained by a preparation method that entails mixing and pulverizing the respective ingredients, adding water and further mixing and/or drying to reach the desired result. Preparation of one of the inventive formulations in the form of a tablet can be achieved by mixing the respective ingredients of the poison bait composition and then compressing the mixture into a tablet form utilizing a suitable tablet press.

The poison bait compositions of the present invention are preferably formulated into a paste formulation in a gel phase, such as gelled poison bait compositions, based on the ease of preparation of such formulations in the controlling of pests, and the ability of such compositions to be applied in a precise manner to the location or habitat of the objective pests being controlled. As such, the gelled poison bait compositions contains an amount of water that typically depends on the amount of molasses in the gelled poison bait compositions, but usually contain water in an amount about from 15% to 50% by weight, based on the total weight of the provided gelled poison bait compositions.

The poison bait compositions of the present invention may be employed in various methods to control objective pests, and an example of such a pest controlling method includes setting, placing or applying an effective amount of one of the poison bait compositions of the present invention in a location that the objective pests inhabit or are otherwise present. When the poison bait compositions are employed in such a method, examples of said locations where the poison bait composition may be set include private residences (e.g., homes and apartments) and commercial areas (e.g., warehouses) and more particularly dining and kitchen areas of homes, as well as areas under various machinery found in residential and/or commercial settings (e.g., computers, copy machines, telephones and vending machines). Even so, it is noted that the present invention is not limited to a method of controlling pests in such specific locations, since it is known to those skilled in the art that pests may inhabit additional locations, where the poison bait compositions and methods of the present invention would be applicable.

In particular, the present inventive methods allow for the poison bait compositions of the present invention to be set, placed, applied, dispersed, spread or sprinkled in any location where the objective pests inhabit or are otherwise present, with the effective amount of the poison bait composition being utilized in such methods depending on the type and amount of the pesticidal active ingredient present in the provided poison bait composition. However, typically a poison bait composition of the present invention is employed in an amount such that about 0.5 g to 5 g of the pesticidally active ingredient in the poison bait composition is employed per 1 $m^2$ of area where the poison bait composition is being utilized to control objective pests.

The present poison bait compositions of the present invention are suited for controlling ants (Formicidae) such as *Monomorium intrudeus* and *Formica japonica*, death watch beetles (Anabiidae) such as the tobacco beetle (*Lasioderma serricorne*) and biscuit beetle (*Stegobium paniceum*), Tenebrionid beetles (Tenebrionidae) such as the red flour beetle (*Tribolium castaneum*) and confused flour beetle (*Tribolium confusum*), flat bark beetles (Cucujidae) such as the sawtoothed grain beetle (*Oryzaephilus surinamensis*) and flat grain beetle (*Cryptolestes pusillus*), termites (Isoptera) such as the Formosan subterranean termite (*Coptotermes formosanus*) and *Reticulitermes speratus*, and is particularly well suited to control cockroaches (Dictyoptera) such as the American cockroach (*Periplaneta americana*), German cockroach (*Blattella gennanica*) and smokybrown cockroach (*Periplaneta fuliginosa*), but is not limited thereto.

EXAMPLE

Example 1

Table I sets forth 3 samples of poison bait compositions of the present invention in parts by weight. Each sample is formulated by mixing the ingredients given in Table I. Sample #1 includes all the ingredients given in Table I, while Sample #2 excludes glycerin and Sample #3 excludes κ-carrageenan. The microencapsulated fenitrothion listed in Table I is an aqueous suspension of microencapsulated fenitrothion (a formulation which microencapsulates by use of a polyurethane wall, produced by Sumitomo Chemical Company), wherein the content of fenitrothion is 20% by weight and the content of water is about 68% by weight, based on the weight of said suspension.

TABLE I

Composition of the Samples in parts by weight

| Sample # | Sample #1 | Sample #2 | Sample #3 |
|---|---|---|---|
| Ingredients | | | |
| Microencapsulated fenitrothion (20%) | 25 | 25 | 25 |
| κ-Carrageenan | 6 | 6 | — |
| Glycerin | 5 | — | 5 |
| Molasses | 37 | 37 | 37 |
| Dextrin | 17 | 17 | 17 |
| Sesame oil | 5 | 5 | 5 |
| Peanut butter | 5 | 5 | 5 |

Solid feeding materials for animals, water (i.e., wetted absorbent cotton), a hiding shelter wherein 3 pieces of veneer were assembled into a triangular tube shape that has a 15 cm length and 3.5 cm width, and 10 of each male and female German cockroaches were inserted into a 27.8 cm×39.8 cm×height 7.5 cm plastic container and left overnight so that the cockroaches could acclimatize to said shelter. Subsequently, 0.5 g of a poison bait sample according to Table I was inserted in said plastic container, and 6 hours later, the poison bait composition that remained after such time was removed from said plastic container. Two (2) days later, a 100% mortality of the German cockroach was observed in the test that utilized Sample #1 as a gelled poison bait of the present invention, and a 80% mortality of German cockroach was observed for the test that utilized Sample #2 or #3 as a poison bait.

Example 2

Table II sets forth 3 samples of poison bait composition in parts by weight. Each sample is formulated by mixing the ingredients given in Table II. Sample #4 includes all the ingredients given in Table II, while Sample #5 excludes glycerin and Sample #6 excludes κ-carrageenan. The microencapsulated fenitrothion listed in Table II is an aqueous suspension of microencapsulated fenitrothion (a formulation which microencapsulates by use of a polyurethane wall, produced by Sumitomo Chemical Company), wherein the content of fenitrothion is 20% by weight and the content of water is about 68% by weight, based on the weight of said suspension.

TABLE II

| Composition of Samples in parts by weight | | | |
|---|---|---|---|
| Sample # | Sample #4 | Sample #5 | Sample #6 |
| Ingredients | | | |
| Microencapsulated fenitrothion (20%) | 25 | 25 | 25 |
| κ-Carrageenan | 6 | 6 | — |
| Glycerin | 5 | — | 5 |
| Molasses | 35 | 35 | 35 |
| Flour | 17 | 17 | 17 |
| Sesame oil | 5 | 5 | 5 |
| Peanut butter | 5 | 5 | 5 |
| Potassium sorbate | 2 | 2 | 2 |

Solid feeding material for animals, water (i.e., wetted absorbent cotton), a hiding shelter wherein 3 pieces of veneer were assembled into a triangular tube shape that has a 15 cm length and 5 cm width, and 10 of each male and female American cockroaches were inserted into a 27.8 cm×39.8 cm×height 7.5 cm plastic container and left overnight so that the cockroaches could acclimatize to said shelter. Subsequently, 1 g of a sample according to Table II was inserted in said plastic container, and 6 hours later, the poison bait composition that remained after such time was removed from said plastic container. Two (2) days later, a 100% mortality of the American cockroach was observed in the test that utilized Sample #4 as a gelled poison bait of the present invention, a 75% mortality of the American cockroach was observed for the test that utilized Sample #5 as a poison bait, and a 80% mortality of the American Cockroach was observed for the test that utilized Sample #6 as a poison bait.

The above test results show that a poison bait composition of the present invention is extremely effective in controlling objective pests, and that such advantageous results are not achieves when either the carrageenan or glycerin components of the inventive poison bait compositions are removed thereform.

What is claimed is:

1. A poison bait composition, comprising
   (1) about 0.05% to 10% by weight of a pesticidally active ingredient,
   (2) about 1% to 10% by weight of a carrageenan,
   (3) about 1% to 10% by weight of glycerin, and
   (4) about 40% to 85% by weight of a powdered crop, dextrin, a sugar, a fat, a fatty oil or a mixture thereof;
   wherein said weight percentages are based on the total weight of said poison bait composition.

2. The poison bait composition according to claim 1, which is a gelled composition and additionally comprises from about 15% to 50% by weight of water, wherein said weight percentages are based on the total weight of said poison bait composition.

3. The poison bait composition according to claim 2, wherein the carrageenan is a κ-carrageenan.

4. A poison bait composition, comprising
   (1) about 0.05% to 10% by weight of a pesticidally active ingredient,
   (2) about 1% to 10% by weight of a carrageenan,
   (3) about 1 % to 10% by weight of glycerin,
   (4) about 5% to 20% by weight of a fat or a fatty oil, and
   (5) about 30% to 80% by weight of a powdered crop, dextrin or a sugar;
   wherein said weight percentages are based on the total weight of said poison bait composition.

5. A method for controlling a pest which comprises setting, placing, applying, dispensing, spreading or sprinkling an effective amount of a poison bait composition in a location that said pest inhabits or is otherwise present, the poison bait composition comprising:
   (1) about 0.05% to 10% by weight of a pesticidally active ingredient,
   (2) about 1% to 10% by weight of a carrageenan,
   (3) about 1% to 10% by weight of a glycerin, and
   (4) about 40% to 85% by weight of a powdered crop, dextrin, a sugar, a fat, a fatty oil or a mixture thereof,
   wherein said weight percentages are based on the total weight of said poison bait composition.

6. The method for controlling a pest according to claim 5, wherein said poison bait composition is a gelled composition and additionally comprises from about 15% to 50% by weight of water, wherein said weight percentages are based on the total weight of said poison bait composition.

7. The method for controlling a pest according to claim 6, wherein said carrageenan is a κ-carrageenan.

8. The method for controlling a pest according to claim 5, wherein said poison bait composition is applied in said location in an amount that applies about 0.5 g to 5 g of the pesticidally active ingredient per 1 $m^2$ of said location.

9. The method for controlling a pest according to claim 5, wherein the pest is a cockroach.

10. A method for controlling a pest which comprises setting, placing, applying, dispensing, spreading or sprinkling an effective amount of a poison bait composition in a location that said pest inhabits or is otherwise present, the poison bait composition comprising:
   (1) about 0.05% to 10% by weight of a pesticidally active ingredient,
   (2) about 1% to 10% by weight of a carrageenan,
   (3) about 1% to 10% by weight of glycerin,
   (4) from about 5% to 20% by weight of a fat or a fatty oil and
   (5) from about 30% to 80% by weight of a powdered crop, dextrin or a sugar;
   wherein said weight percentages are based on the total weight of said poison bait composition.

* * * * *